(12) United States Patent
Yoshida et al.

(10) Patent No.: US 6,943,876 B2
(45) Date of Patent: Sep. 13, 2005

(54) METHOD AND APPARATUS FOR DETECTING PATTERN DEFECTS

(75) Inventors: Minoru Yoshida, Yokohama (JP); Sachio Uto, Yokohama (JP); Shunji Maeda, Yokohama (JP); Toshihiko Nakata, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 394 days.

(21) Appl. No.: 10/223,423

(22) Filed: Aug. 20, 2002

(65) Prior Publication Data

US 2003/0227617 A1 Dec. 11, 2003

(30) Foreign Application Priority Data

Jun. 7, 2002 (JP) ...................................... 2002-166456

(51) Int. Cl.[7] .............................................. G02N 21/88
(52) U.S. Cl. ................... 356/237.2; 356/237.5
(58) Field of Search ...................... 356/237.1–237.5, 356/239.1, 394; 250/372, 559.44

(56) References Cited

U.S. PATENT DOCUMENTS

| | | | | |
|---|---|---|---|---|
| 4,812,748 A | * | 3/1989 | Brust et al. .................. | 250/311 |
| 4,930,896 A | * | 6/1990 | Horikawa .................... | 356/609 |
| 5,649,022 A | * | 7/1997 | Maeda et al. ................ | 382/141 |
| 5,764,363 A | * | 6/1998 | Ooki et al. .................. | 356/364 |
| 5,774,222 A | * | 6/1998 | Maeda et al. ................ | 356/394 |
| 5,932,871 A | * | 8/1999 | Nakagawa et al. ....... | 250/201.3 |
| 6,091,075 A | * | 7/2000 | Shibata et al. .......... | 250/559.44 |
| 6,556,290 B2 | * | 4/2003 | Maeda et al. ............ | 356/237.2 |
| 6,621,571 B1 | * | 9/2003 | Maeda et al. ............ | 356/237.5 |
| 6,800,859 B1 | * | 10/2004 | Shishido et al. ............ | 250/372 |
| 2003/0095251 A1 | * | 5/2003 | Maeda et al. ............ | 356/237.2 |
| 2005/0083519 A1 | * | 4/2005 | Maeda et al. ............ | 356/237.2 |

FOREIGN PATENT DOCUMENTS

| | | |
|---|---|---|
| JP | 61-212708 | 9/1986 |
| JP | 8-320294 | 12/1996 |
| JP | 11-271213 | 10/1999 |

* cited by examiner

*Primary Examiner*—Hoa Q. Pham
(74) *Attorney, Agent, or Firm*—Antonelli, Terry, Stout & Kraus, LLP

(57) ABSTRACT

A method and apparatus for detecting pattern defects which includes annularly scanning of a laser beam emitted from a laser light source on a pupil of an objective lens, illuminating the scanned laser beam, through the objective lens, onto a sample on which there is formed a pattern coated with an optically transparent thin film, acquiring an optical image of the illuminated sample, and processing the acquired image to find defects in the pattern. The annular scan diameter of the laser beam is determined based on the thickness of the optically transparent thin film.

15 Claims, 18 Drawing Sheets

FIG.17
(a)
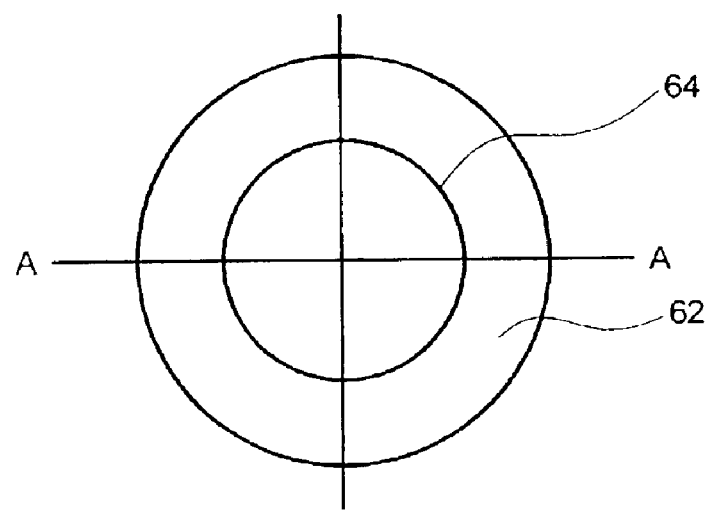
(b)
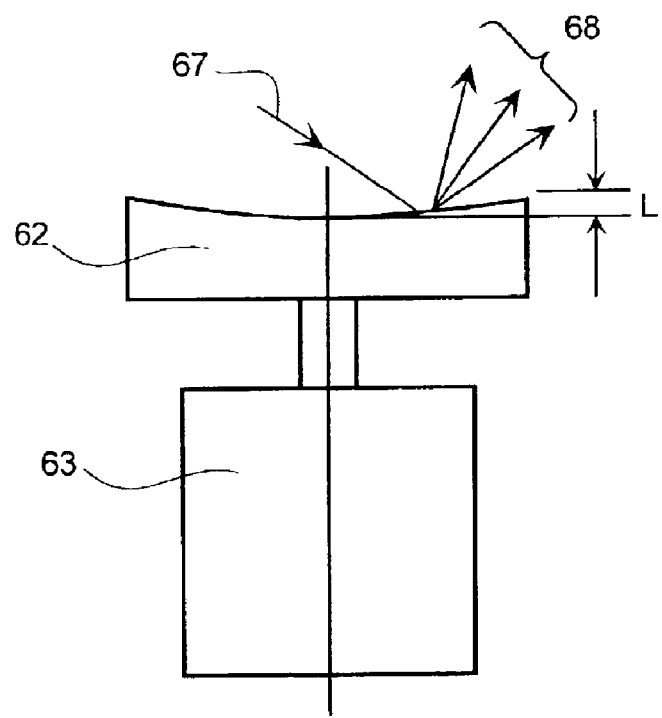

METHOD AND APPARATUS FOR DETECTING PATTERN DEFECTS

BACKGROUND OF THE INVENTION

The present invention relates to pattern defect inspection methods and apparatus using a laser beam as illumination light, mainly for inspecting and observing micro pattern defects or foreign matter contamination occurring in manufacturing processes for semiconductor devices and flat panel displays.

Circuit patterns tend to continually become finer and smaller as semiconductor devices become more highly integrated. Smaller and finer circuit patterns have spurred a demand for higher resolution when inspecting for defects of circuit patterns that have been formed on semiconductor wafers by photolithographic processes using photomasks or reticles. One technique for enhancing resolution when detecting pattern defects involves the use of illumination light on shorter wavelengths from visible light to ultraviolet light. Mercury lamps and xenon lamps, for example, have been conventionally used as illumination light sources, while only the required wavelengths are optically selected and utilized from among the various line spectra emitted from these lamps.

Illumination from a typical light source lamp, however, contains only a few line spectra in the ultraviolet region. A larger size lamp with higher power must therefore be used to obtain a sufficient light intensity, but this results in the problem of lower lighting efficiency. Yet another problem is that correcting the chromatic aberration of optical systems used for pattern inspection is difficult due to the wide spectral bandwidth.

Optical aligners of this type used in semiconductor device manufacturing also require high resolution. For this reason, optical aligners equipped with a krypton fluoride (KrF) excimer laser that emits light at a 248 nm wavelength are mainly used. Optical aligners using an argon fluoride (ArF) excimer laser that emits an even shorter 193 nm wavelength have also been developed. However, these excimer lasers are large in size and use fluorine gases that are armful to the human body, so specified safety measures must be implemented.

Recently, a great deal of attention is being focused on solid-state YAG lasers as another type of ultraviolet laser. YAG lasers are capable of generating a third harmonic (355 nm wavelength) or fourth harmonic (266 nm wavelength) by wavelength conversion when the laser beam is passed through a nonlinear optical crystal. This has led to the development of compact, easy to handle ultraviolet lasers. These compact and easy to use ultraviolet lasers are highly effective for use in a pattern inspection apparatus.

Laser beams have superior coherence, but this causes enhancement and attenuation in the light flux when they are used to illuminate a sample, and such illumination produces an interference fringe on the sample. In a pattern inspection apparatus using a laser, as disclosed in Japanese Patent JP-A No. 271213/1999, a light beam emitted from a laser light source is guided into a fly-eye lens (micro-lens array) to form a multi-spot light source. This multi-spot light source is focused so as to strike a sample under test so that the sample is uniformly illuminated with light. The intensity of the light reflecting from the sample is then detected with a charge integration type of CCD line sensor.

The aforesaid pattern defect inspection apparatus using a laser has the following problems.

The light beam emitted from the laser is transformed into a multi-spot light source by a fly-eye lens and is focused by a condenser lens so as to illuminate the entire area of the sample under test. The incident angle of the illumination light on the surface of the sample under test is determined by the focal positions of the fly-eye lens and the condenser lens. When a thin film is formed on the surface of the sample, the light reflected from the sample contains light components reflecting from the surface of the thin film and also light reflecting from the lower layer surface of the thin film after penetrating into the thin film. Thus, the phase of the light reflecting from the lower layer surface of the thin film changes on the surface of the thin film according to the thickness of the thin film, so that the reflected light intensity to be detected on the surface of the sensor will vary.

Now we will discuss how the intensity of reflected light changes in cases where a thin film, such as an insulating film, is formed on the surface of a sample. A typical interference model is shown in FIG. 6. Here, the wavelength of illumination light 37 is set as λ, the incident angle of the illumination light 37 relative to the normal line direction on the surface of the sample is θ, the refractive index of the air layer 34 is n0, the thickness and refractive index of the thin film 35 are t1 and n1, respectively, and the refractive index of the semiconductor substrate 36 is n2. If the intensity of light reflected 38 reflected from the surface of the thin film 35 is set as r01, and the intensity of light 39 reflected from the substrate 36 after passing through the thin film 35 is r12, then the composite reflected light can be defined as R. These factors can be theoretically modeled as Fresnel equations and expressed by the following equations 1 to 4. An example of the calculated results is shown in FIG. 7, wherein the horizontal axis represents the thickness of the thin film 35 and the vertical axis represents the composite light intensity R. Changes in the composite light intensity versus the film thickness, when plotted, result in waveform 40.

$$X = \frac{4\pi n1 t1}{\lambda} \quad \text{(Eq. 1)}$$

$$r01 = \frac{n1 - n0}{n1 + n0} \quad \text{(Eq. 2)}$$

$$r12 = \frac{n2 - n1}{n2 + n1} \quad \text{(Eq. 3)}$$

$$R = \frac{r02^2 + r12^2 + 2r01 r12 \cos(X)}{1 + r01^2 r12^2 + 2r01 r12 \cos(X)} \quad \text{(Eq. 4)}$$

FIG. 8 shows a cross section of a sample on which circuit patterns are formed. A circuit 41 and a circuit 42 are formed on a semiconductor substrate 36, and the entire surface of the sample is covered with an insulating film 35. Assuming, for example, that the circuit 41 has a low density pattern, while the circuit 42 has a high density pattern, and also that the thickness of the insulating film 35 is not uniform for some reason, the thickness of the insulating film 35 will be tb on the circuit 41 and t11 on the circuit 42. As mentioned above, if the thickness of the insulating film 35 varies, then the light reflected from the sample, which contains a light component reflecting from the thin film surface and a light component reflecting from the thin film lower layer surface (after penetrating into the thin film), changes accordingly. FIG. 9 shows this change in the reflected light intensity caused by the example of FIG. 8. The difference in reflected light intensity between the thickness t10 and thickness t11 of the insulating film 35 corresponds to a portion 44 on a waveform 43, that indicates the relation between the reflected light intensity and the film thickness. A change (Rt1) can be observed in the reflected light intensity. When the pattern of the sample is inspected under this condition, the change in the reflected light intensity caused by the difference in the transparent film thickness is detected as a change in brightness.

In inspection methods used heretofore, a sample is illuminated with light incident on the sample at a certain angle. So, when the thickness of a transparent film formed over the surface of the pattern varies at different position's, the reflected light intensity from the sample, which contains light components reflecting from the surface of the transparent film and also light components reflecting from the lower layer surface of the transparent film, changes according to the position on the film, and so an interference fringe pattern occurs. Due to this interference fringe pattern, the reflected light intensity to be detected on a CCD line sensor varies according to the position on the thin film. To reduce adverse effects from uneven brightness or shading caused by the interference fringe pattern, the CCD line sensor must be adjusted so as to detect dark areas, and, as a result, the detection sensitivity is reduced to a lower level.

SUMMARY OF THE INVENTION

The present invention has the object of providing an optical system which is able to uniformly illuminate a sample without being affected by variations in the thickness of a transparent thin film formed over the surface of the sample, even when using a monochromatic light source, such as a laser, as well as providing a highly reliable pattern defect inspection method and apparatus that ensure highly accurate inspection without lowering the detection efficiency.

In the pattern defect inspection method of the present invention, a laser beam that is emitted from a laser light source annularly scans on the pupil plane of an objective lens. This annularly scanning laser beam is irradiated onto a sample (pattern formed on a semiconductor substrate and covered with an optically transparent thin film). An optical image of the sample that has been produced by the laser irradiation is acquired by an image sensor, and this optical image is then processed to find defects in the pattern. In this pattern inspection process, the annular scan diameter of the laser beam is determined on the basis of the thickness of the optically transparent thin film.

In accordance with the present invention, when a pattern formed on a semiconductor substrate is inspected through an optically transparent thin film coated over the pattern, a laser beam emitted from a laser light source annularly scans on the pupil plane of an objective lens, and then it illuminates the pattern on the semiconductor substrate that is placed on a table that is continuously moving along one direction. An optical image of the pattern thus illuminated is then acquired in synchronization with the annular scan of the laser beam. Defects in the pattern can be detected by processing this image.

These and other objects, features and advantages of the invention will be apparent from the following detailed description of preferred embodiments of the invention, as illustrated in the accompanying drawings.

BRIEF DESCRIPTION OF THE DRAWINGS

FIG. 17(a) is a diagram showing a front view of the mirror shown in FIG. 16;

FIG. 17(b) is a diagram showing a side view of the mirror shown in FIG. 16;

DESCRIPTION OF THE PREFERRED EMBODIMENTS

Preferred embodiments of a high-resolution optical system and a pattern defect inspection apparatus of the present invention will be described in detail with reference to the accompanying drawings.

Figure 1:
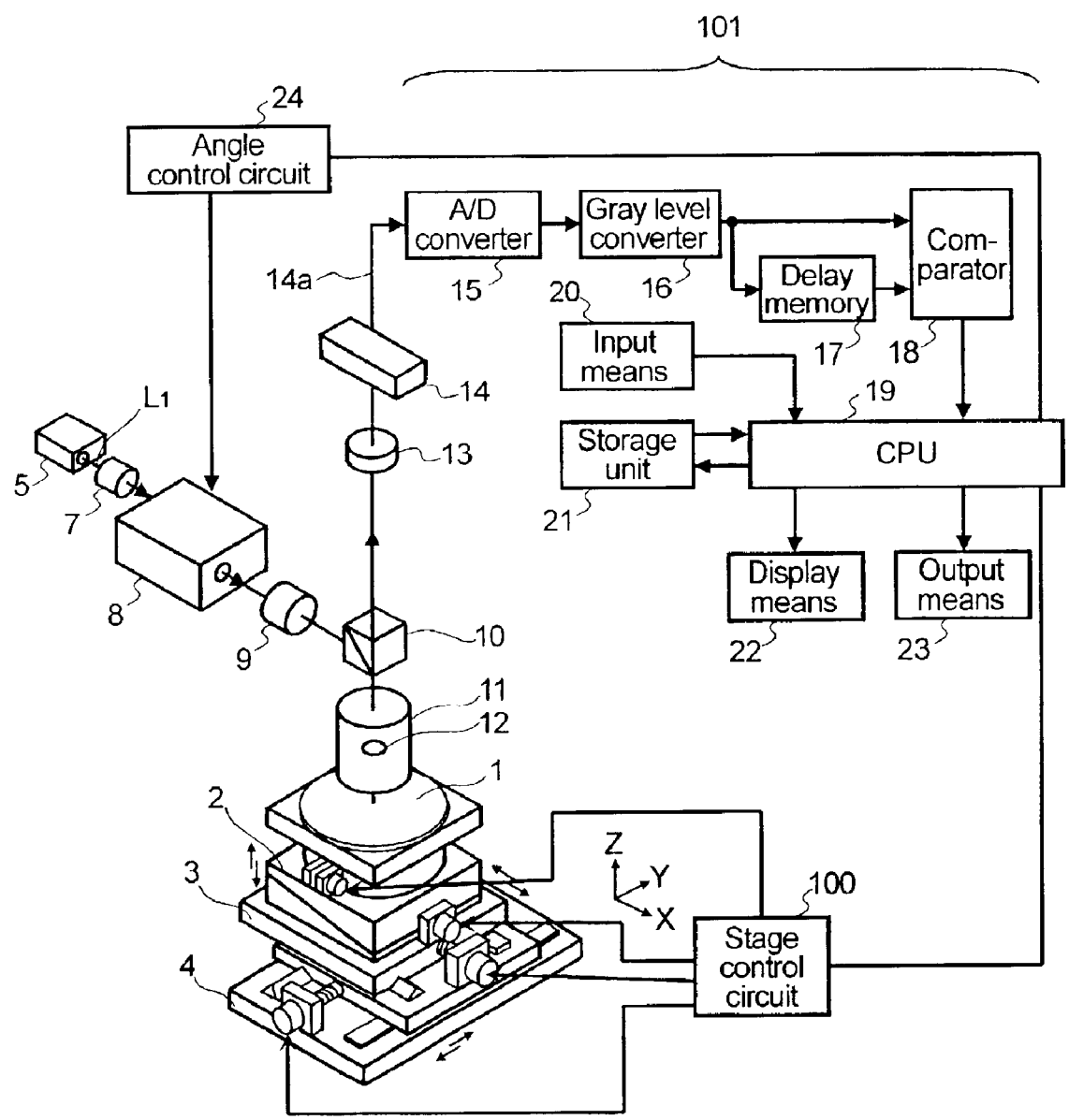
FIG. 1 is a schematic diagram showing a pattern defect inspection apparatus representing a first embodiment of the present invention.

FIG. 1 is a schematic diagram showing a pattern defect inspection apparatus representing a first embodiment of the present invention. Reference numeral 1 in FIG. 1 denotes a sample constituted, for example, by a semiconductor wafer (device under test) on which there is fabricated a circuit pattern to be inspected. The sample 1 is placed and held on a Z stage 2 (by means, for example, of a vacuum chuck or electrostatic chuck that is not shown in the drawing) that moves in the Z direction and rotates. A Y stage 4 and an X stage 3 can be independently moved to any desired position under control from a stage control circuit 100. The position of each stage is constantly detected by a length measuring device or position sensor (not shown in the drawing). The detected position data, indicative of the position of the X stage 3 and Y stage 4, is input to a central processing unit (CPU) 19. The stage control circuit 100 is connected to the central processing unit 19.

The present invention employs an ultraviolet laser light source (ultraviolet laser generator) 5 that emits a far ultraviolet laser beam to illuminate the sample with far ultraviolet light of high intensity. A laser beam L1, that is emitted from the ultraviolet laser light source 5, is guided into an objective lens 11 by way of a beam expander 7, coherence suppression optics 8, lens 9, and a beam splitter 10, and it then illuminates the sample 1. The beam expander 7 enlarges the ultraviolet laser beam to a certain diameter. The enlarged laser beam is condensed by the lens 9 onto a position near the pupil 12 of the objective lens 11, and it then illuminates the sample 1.

The light reflecting from the sample 1, when the sample is illuminated with the laser beam L1, is focused onto the photosensitive surface of an image sensor 14 by way of the objective lens 11, beam splitter 10, and focusing lens 13, which are perpendicularly installed above the sample 1, and an optical image of the sample 1 is thus obtained. The image sensor 14, for example, can be a charge integration type sensor (time delay integration type image sensor: abbreviated to TDI sensor), which is capable of detecting ultraviolet light, and it outputs a grayscale image signal according to the brightness (gray level) of the light reflecting from the pattern formed on the sample 1 under test.

Figure 20:
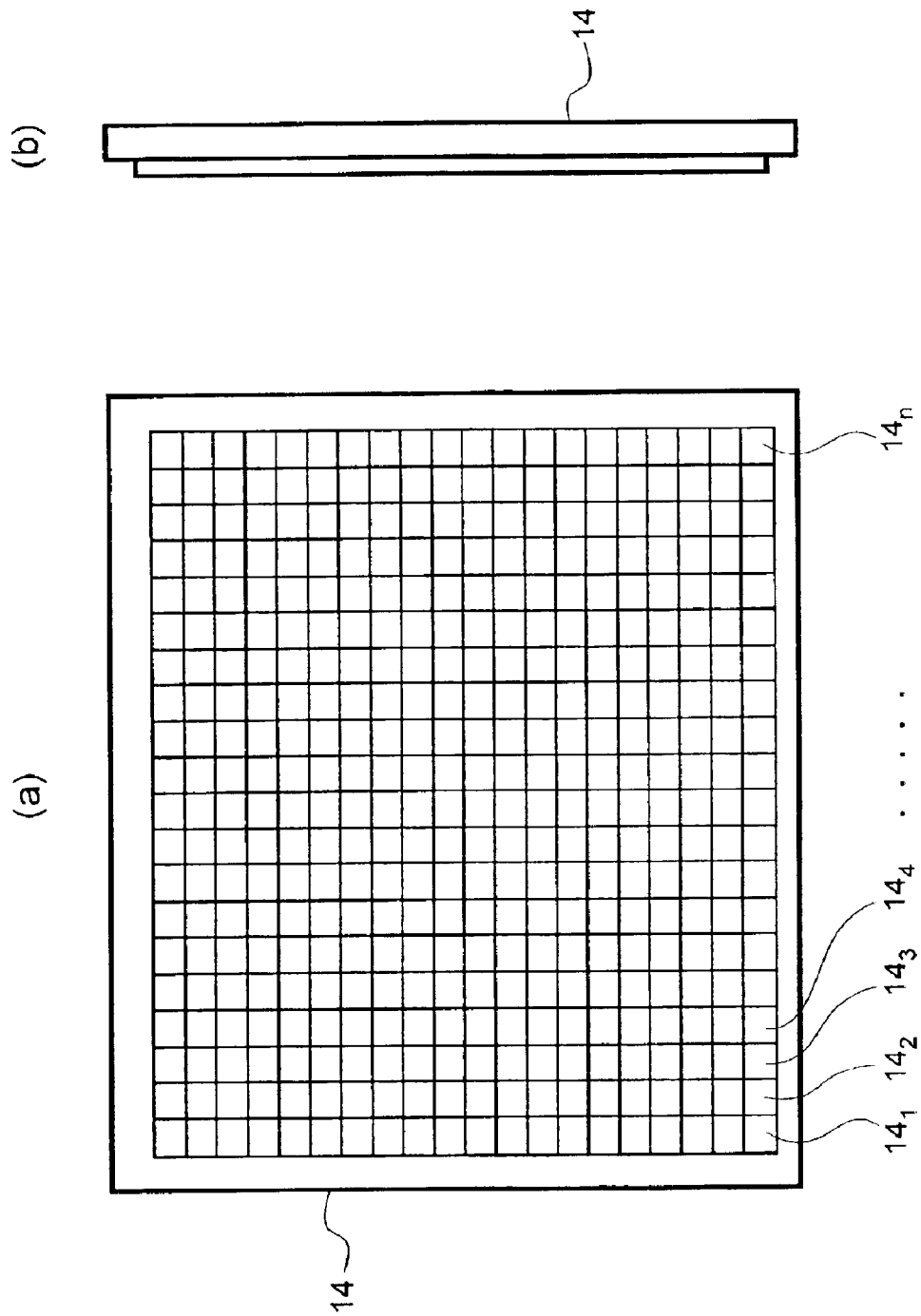
FIG. 20(a) is a schematic diagram showing a front view of the TDI (time delay integration) image sensor.
FIG. 20(b) is a schematic diagram showing a side view of the TDI (time delay integration) image sensor.

The TDI sensor 14 is made up of an array of linear image sensors connected in a multistage configuration, as shown in FIG. 20(a) and FIG. 20(b). The sample 1 is first viewed with the first stage linear image sensor $14_1$ in synchronization with movement of the Y stage, which continuously moves in response to a control signal from the central processing unit 19. The signal obtained here is transferred to the second stage linear image sensor $14_2$. Next, when the area on the sample 1, whose image was acquired with the first stage linear image sensor $14_1$, moves to the position of the second stage linear image sensor, as a result of movement of the Y stage, the image in that area is again acquired, this time with the second stage linear image sensor $14_2$ and the detected signal here is added to the signal already transferred from the first stage linear image sensor $14_1$. By repeating this process for all of the subsequent stage linear image sensors up to the last stage image sensor $14_n$, the signals detected by each linear image sensor stage are all accumulated and output.

In the above-described apparatus, the central processing unit 19 issues an instruction to the stage control circuit 100 to drive the stage 3, 50 that the sample 1 moves at a constant speed along one direction. At the same time, an optical image of the pattern fabricated on the sample 1 under test is detected with the TDI sensor 14 in synchronization with movement of the stage 3 by utilizing position data indicating the position of the stage 3. This position information is monitored using a length measuring device or position sensor (not shown in the drawing). Brightness information (grayscale image signal) 14a about the pattern formed on the sample 1 is obtained in this way. The grayscale image signal 14a, that is obtained with the image sensor 14, is then input to a signal processing circuit 101 to find pattern defects, including foreign matter deposited on the sample 1 under test. The signal processing circuit 101 is comprised of an A/D converter 15, a gray level converter 16, a delay memory 17, a comparator 18, and the central processing unit 19. The A/D converter 15 converts the grayscale image signal 14a, that has been obtained with the TDI sensor 14, into a digital signal. Here, the AND converter 15 can also be installed at a location immediately after (downstream from) the TDI sensor 14, outside of the signal processing circuit 101. If necessary, the coherence suppression optics 8 can be internally controlled by an angle control circuit 24 from the central processing unit 19.

The gray level converter 16 consists, for example, of an 8-bit gray level converter, and it performs gray level conversion on the digital image signal that has been transferred from the A/D converter 15, as described in JP-A No. 320294/1996. The gray level converter 16 performs this conversion using logarithmic, exponential and polynomial expressions to correct shading or uneven brightness on the image caused by laser beam interference with the thin film formed on the sample 1 under test (such as thin films formed on a semiconductor wafer during a wafer process). The delay memory 17 stores the image signal that has been transferred from the gray level converter 16, within a period of the scan width of the image sensor 14, so as to produce a delay equal to one cell or one chip or one shot comprising the sample (semiconductor wafer).

The comparator 18 compares the image signal transferred from the gray level converter 16 with the image signal obtained through the delay memory 17, in order to detect mismatches between them as defects. In other words, the comparator 18 compares the detected image with an image transferred from the delay memory 17 that was obtained with a delay equal to the cell pitch or to one chip.

The central processing unit (CPU) 19 creates defect inspection data based on inspection results produced by the comparator 18, and also based on coordinate positioning data on the sample 1 (semiconductor wafer). This data is obtainable from circuit design information and should be entered in advance from an input means 20, which consists of a keyboard, storage medium, network, etc. This defect inspection data is stored in the storage unit 21, and it can be displayed on a display means 22 as needed, or it can be output to an output means 23 for observing the locations of defects on other review (evaluation) devices.

Figure 21:
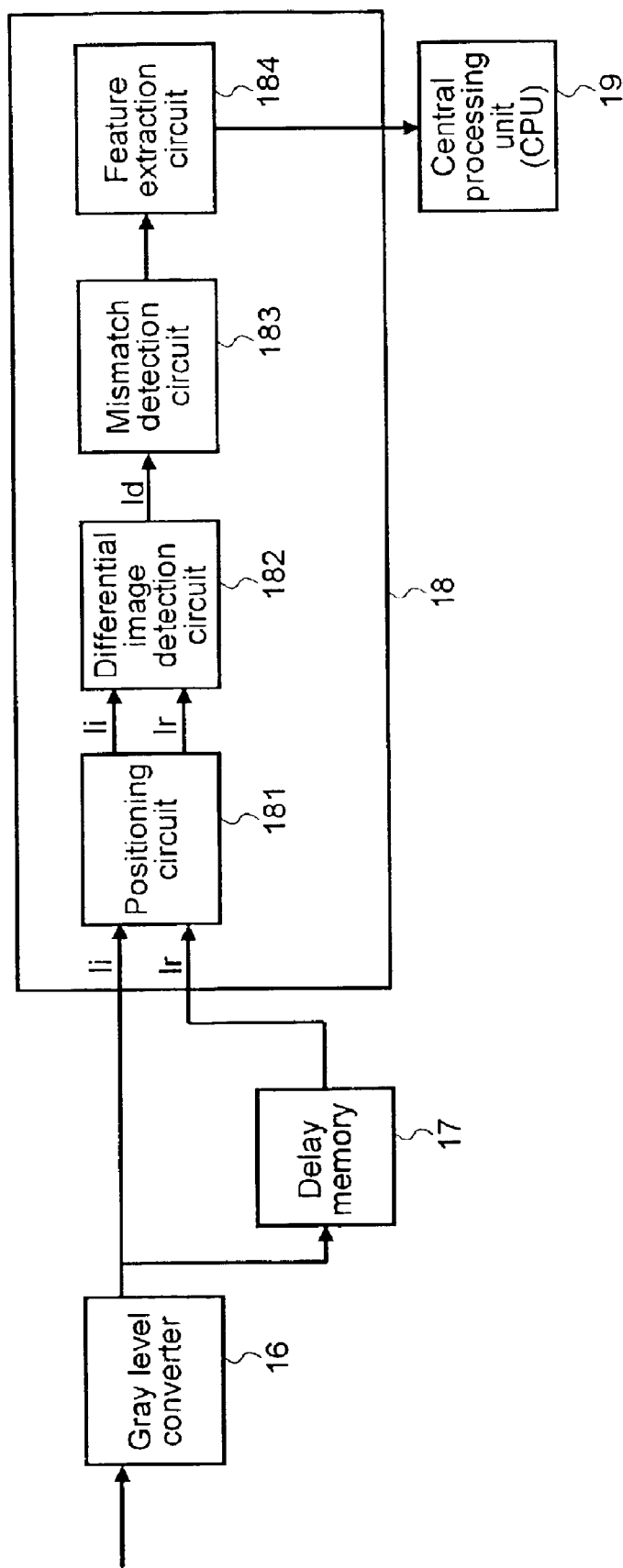
FIG. 21 is a block diagram of comparator 18 shown in FIG. 1.

The comparator 18 can be configured in the manner disclosed in JP-A No. 212708/1986. The comparator 18, as shown in FIG. 21, for example, consists of a positioning circuit 181, that aligns the positions of the comparison image 11, that has been transferred from the gray level converter 16, and the reference image Ir, that has been transferred from the delay memory 17; a differential image detection circuit 182, that detects a differential image Id, that represents the difference between the comparison image 11 and the reference image Ir that were aligned with each other by the positioning circuit 181; a mismatch detection circuit 183 that converts the differential image Id, that has been detected by the differential image detection circuit 182, into a binary image by setting a threshold level; and a feature extraction circuit 184, that extracts information about the area, length and coordinates from the binary output transferred from the mismatch detection circuit 183.

Next, an embodiment of the ultraviolet laser light source (ultraviolet laser generator) 5 will be described. As stated earlier, shorter wavelengths of illumination light are essential to obtain a higher resolution in pattern defect inspection, and the sample 1 also should be illuminated with higher intensity light to improve the inspection speed. Discharge lamps, such as mercury-xenon lamps, have been widely used as illumination light sources for this purpose. Since these discharge lamps produce high intensity in the visible region, the line spectra in the visible region are mainly utilized to obtain higher intensity illumination. Line spectra in the ultraviolet to deep ultraviolet region are only a few percent of those in the visible region, so that a high-power lamp must be used to obtain the required ultraviolet or deep ultraviolet light intensity.

When a larger lamp with higher power is used, the optical system must be separated from the light source to prevent adverse effects from heat generated from the lamp, but this is not always practical because of space limitations. In view of these problems, the invention uses a deep ultraviolet (DUV) laser 5, that emits a DUV laser beam in a wavelength range between 100 and 355 nm.

Lasers are well known as coherent light sources (having coherence), so that, when a laser beam illuminates the circuit pattern formed on the sample 1 under test, speckle noise (interference fringe) occurs, causing trouble during pattern defect inspection. Because of this problem, the invention uses the coherence suppression optics 8 to spatially reduce the coherence of the laser beams and thereby minimize speckle noise.

Figure 2:
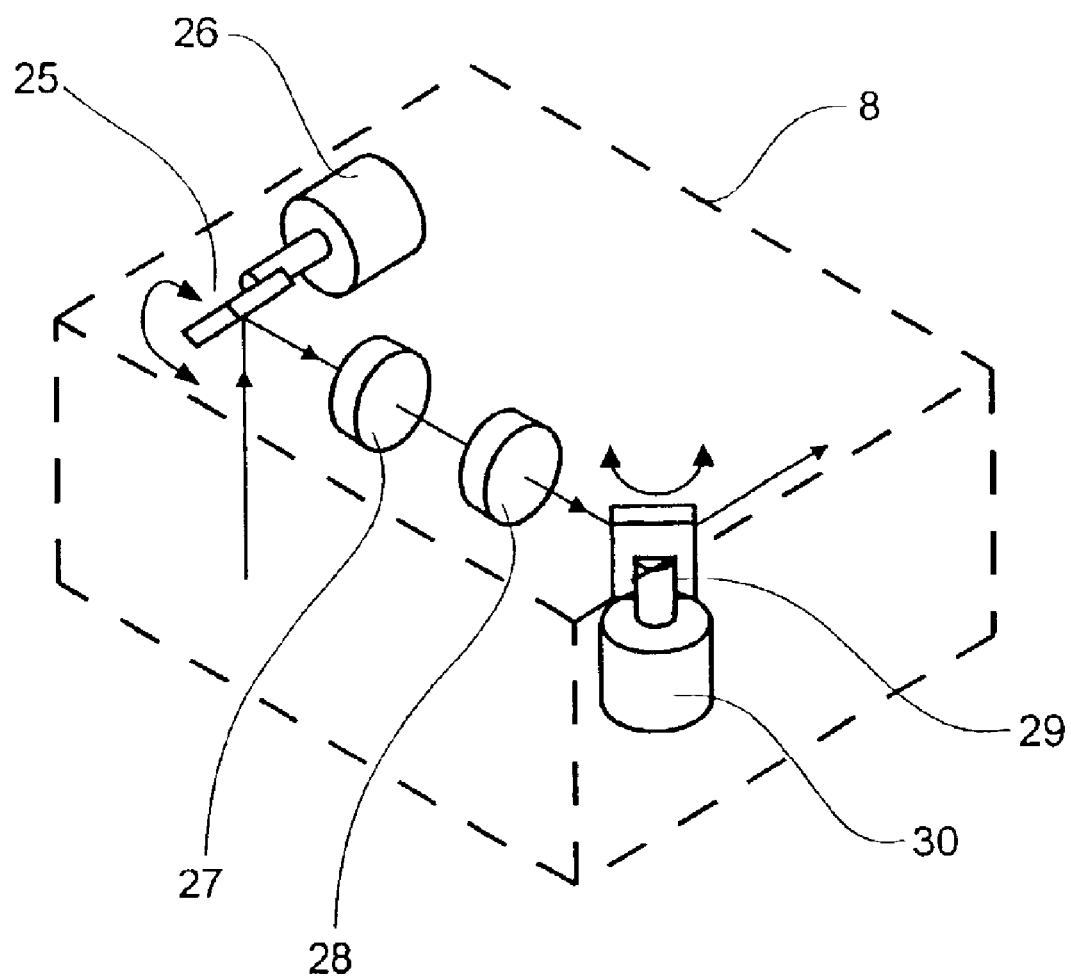
FIG. 2 is a diagram of an embodiment of the light illuminating optical system shown in FIG. 1, including coherence suppression optics.

FIG. 2 is a simplified diagram of one example of the coherence suppression optics 8 of the present embodiment. The laser beam L1, that is emitted from the laser light source 5, strikes a mirror 25. This mirror 25 is driven by an oscillating motor 26 that oscillates the mirror 25 within a small angle. Since the mirror 25 is oscillated by the oscillating motor 26, the optical axis of the laser beam L1 that is reflected from the mirror 25 is scanned along the vertical direction. The laser beam L1, that is reflected from the mirror 25, is then guided to a mirror 29 via lenses 27 and 28. The mirror 29 is driven by another oscillating motor 30 that also oscillates within a small angle, so that the mirror 29 oscillates as well. When the laser beam L1 strikes the mirror 29, the optical axis of the reflected light is scanned along the horizontal direction. The mirrors 25 and 29 are respectively installed at positions conjugate with the focusing position of the objective lens 11.

Figure 3:
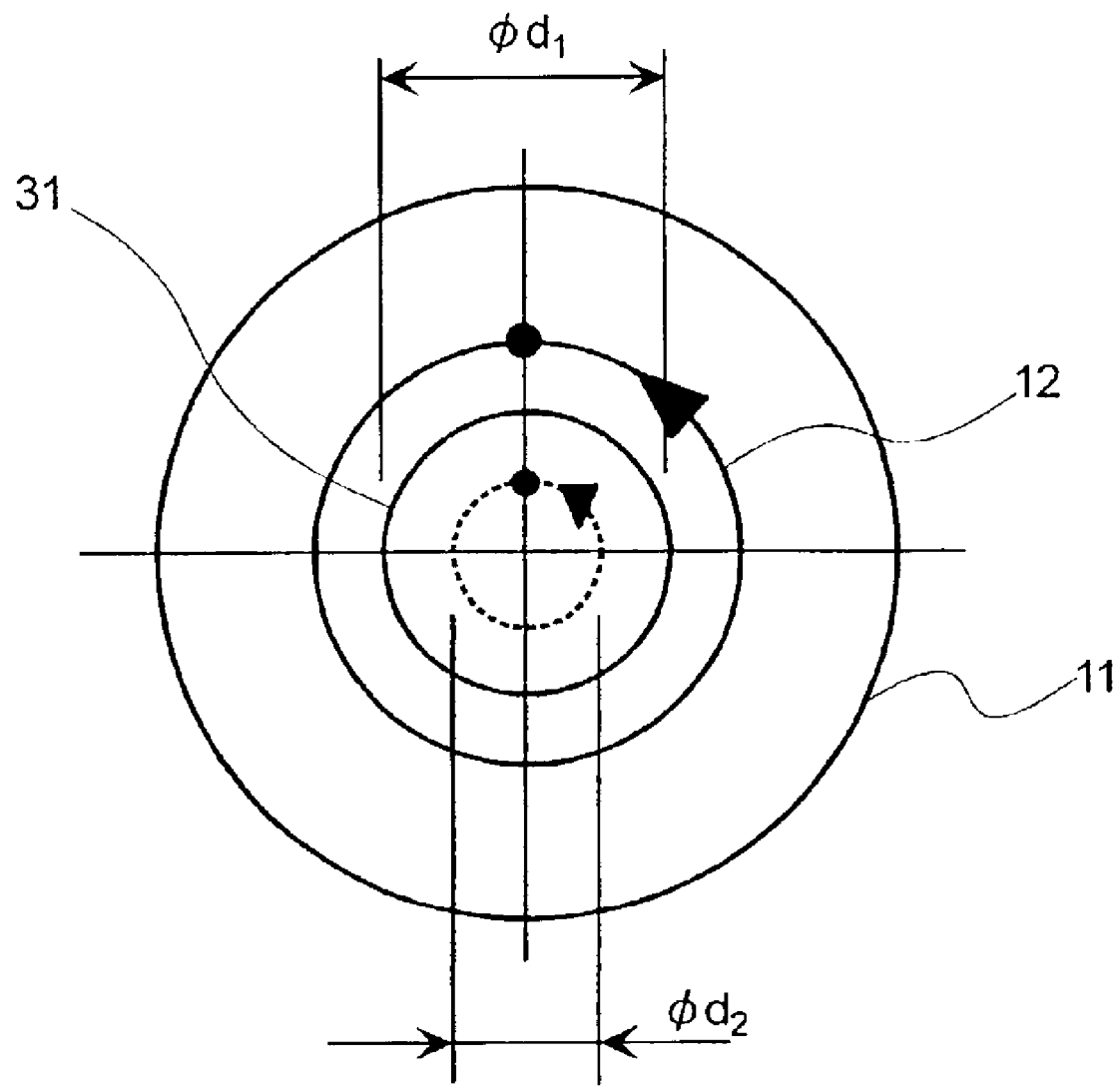
FIG. 3 is a diagram which shows the laser beam scanning on the pupil of an objective lens.
Figure 4:
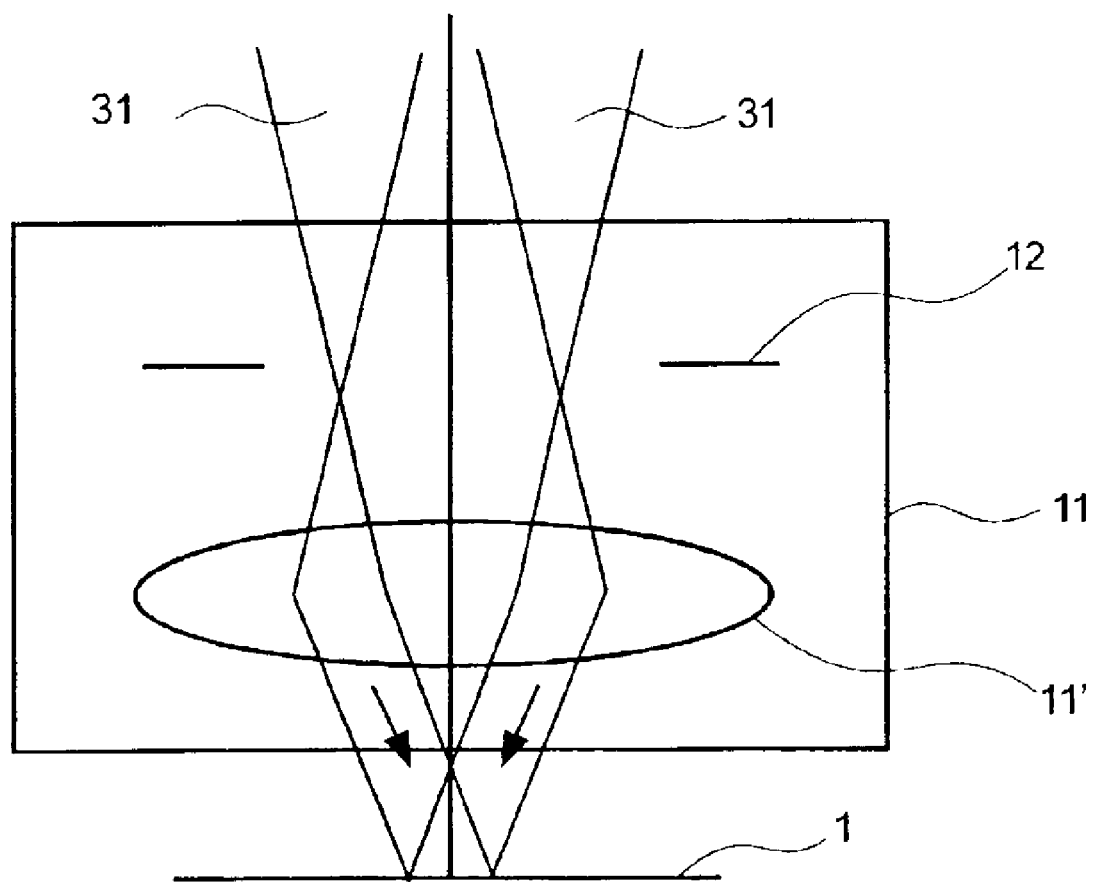
FIG. 4 is a diagram which shows how light flux enters the pupil of an objective lens.

FIG. 3 shows the objective lens 11, as viewed along the optical axis. FIG. 4 is a lateral view of the objective lens 11. The laser beam, that is scanned along the vertical direction by the mirror 25 and also along the horizontal direction by the mirror 29, enters the objective lens 11 as a light flux 31 and is focused on the pupil 12 of the objective lens 11. The light flux 31, that is focused on the pupil 12, enters a lens 11' and then exits from the objective lens 11 as parallel light so as to illuminate the sample 1. In other words, the sample 1 is subjected to Koehler illumination.

Figure 5:
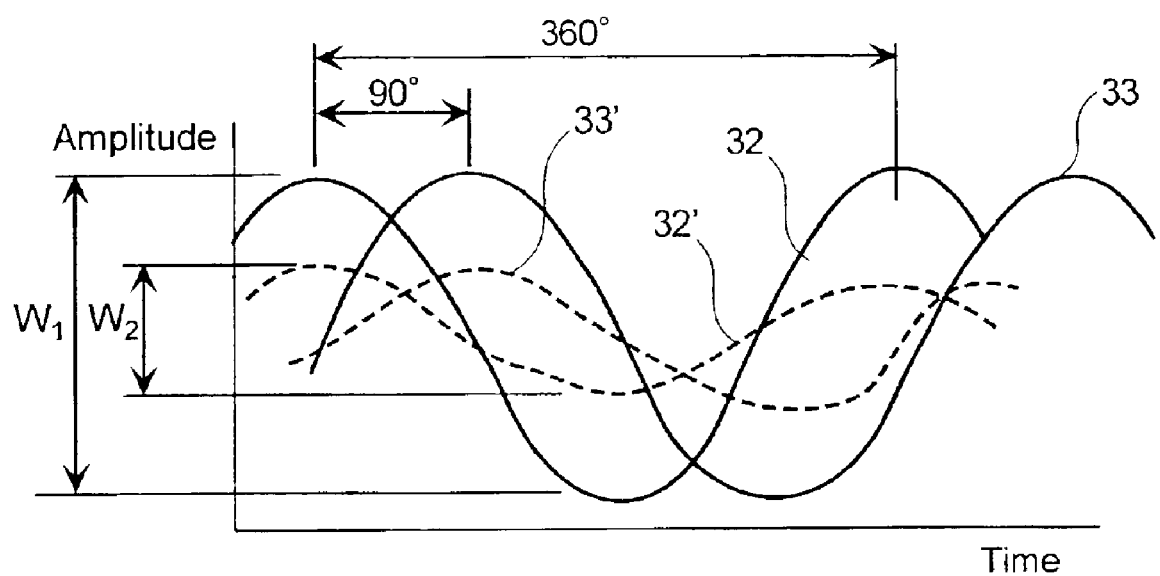
FIG. 5 is a graph which shows waveforms used for directing the coherence suppression optics shown in FIG. 2.

By oscillating the mirrors 25 and 29 in synchronism with each other, the light flux 31 annularly scans on the pupil 12 of the objective lens 11. FIG. 5 shows an example of this operation. The oscillating motor 26 drives the mirror 25 according to a control curve 32, which is usually a sine curve. The oscillating motor 30, on the other hand, drives the mirror 29 according to a control curve 33, which is obtained by shifting the phase thereof by 90° with respect to the control curve 32. Controlling the mirrors 25 and 29 in this way allows the light flux 31 to annularly scan on the pupil 12 of the objective lens 11i. As a result, the sample 1 is illuminated with light whose incident direction continuously changes over time. This prevents interference that occurs by light input from different directions, which tends to reduce the laser beam coherency.

In accordance with the invention, one annular scan cycle of the light flux on the pupil 12 of the objective lens 11 is synchronized with the charge integration time during which each linear image sensor of the TDI sensor 14 stores a signal charge upon detecting light. More specifically, within one integration time, during which each linear image sensor of the TDI sensor 14 stores a signal charge, the light flux 31 annularly scans one or more times on the pupil 12 of the objective lens 11. In addition, the annular scan diameter of the light flux 31 on the pupil 12 can be adjusted by changing the amplitude applied to the oscillating motors 26 and 30. For example, when the oscillating motors 26 and 30 are driven with amplitude W1 shown in FIG. 5, the annular scan diameter on the pupil 12 will be Φd1, as seen in FIG. 3.

When the amplitude is smaller, such as W2 for waveforms 32' and 33', as seen in FIG. 5, the annular scan diameter on the pupil 12 will be Φd2, as seen in FIG. 3.

As explained above, the annular scan diameter of the light flux 31 on the pupil 12 can be freely changed by controlling the amplitude applied to the oscillating motors 26 and 30. The annular scan diameter of the light flux 31 on the pupil 12 may also be changed for each scan when two or more annular scans are repeated within one integration time, during which each linear image sensor of the TDI sensor 14 stores a signal charge.

The operation of a pattern inspection apparatus having the above-described configuration will be described in detail.

Figure 11:
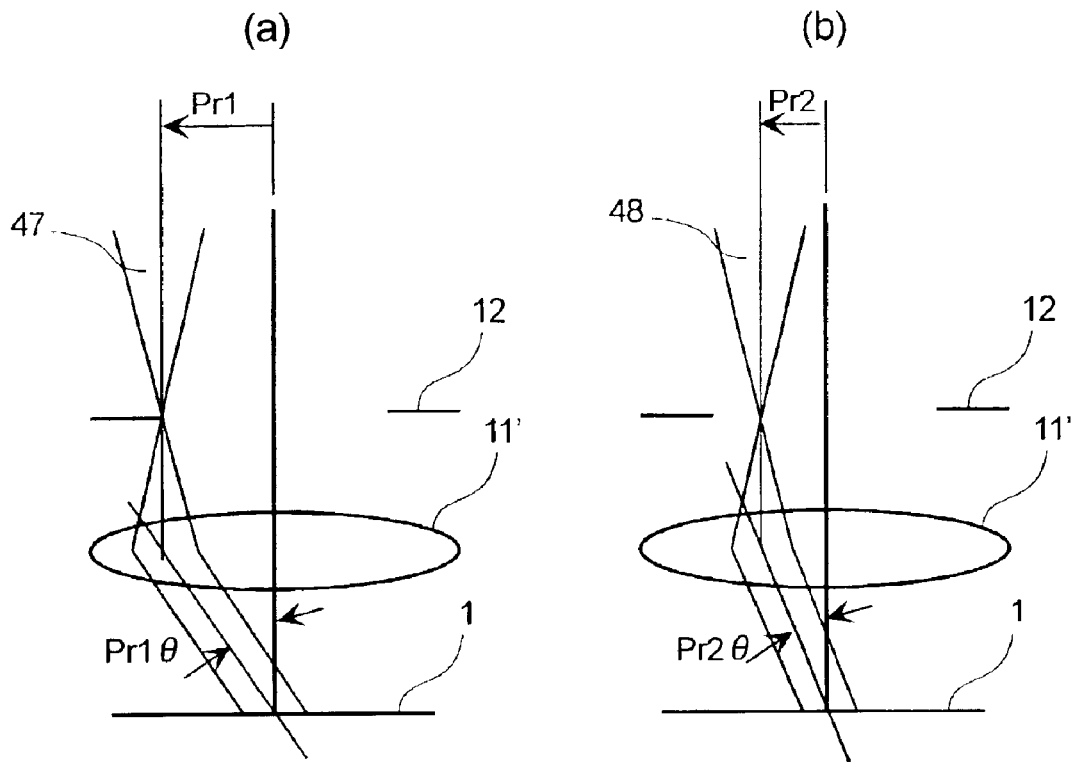
FIG. 11(a) is a diagram which shows the incident angle of a light beam entering near the edge of the objective lens pupil.
FIG. 11(b) is a diagram which shows the incident angle of a light beam entering near the center of the objective lens pupil.

FIGS. 11(a) and 11(b) show how the angle of a light flux illuminating the sample 1 is changed. FIG. 11(a) shows light flux 47 that is caused to annularly scan through a point near the edge of the pupil 12 of the objective lens 11. The main beam of this light flux 47 is at a position Pr1, that is spaced away from the center of the optical axis and is irradiated on the sample at an incident angle of Pr1θ by the lens 11'. FIG. 11(b) shows a light flux 48 that is caused to annularly scan through a point near the center of the pupil 12 of the objective lens 11 by adjusting the amplitude of the oscillating motors 26 and 30. This light flux 47 is irradiated on the sample at an incident angle of Pr2θ by the lens 11'.

Figure 6:
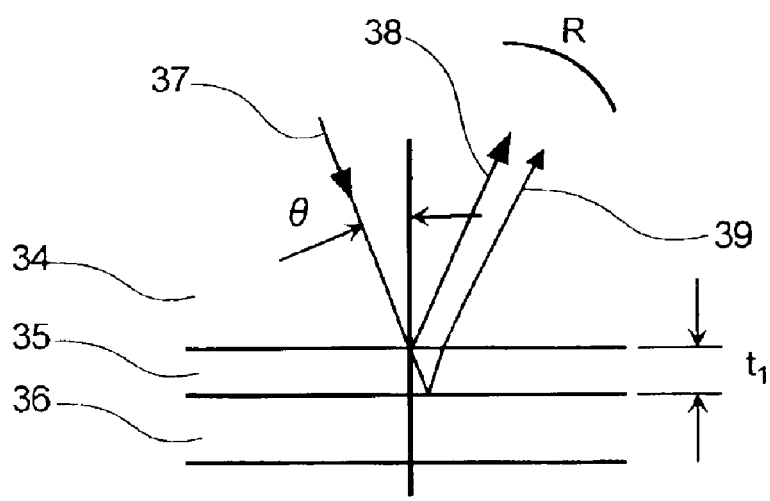
FIG. 6 is a diagrammatic cross section of a semiconductor substrate showing thin film interference.
Figure 7:
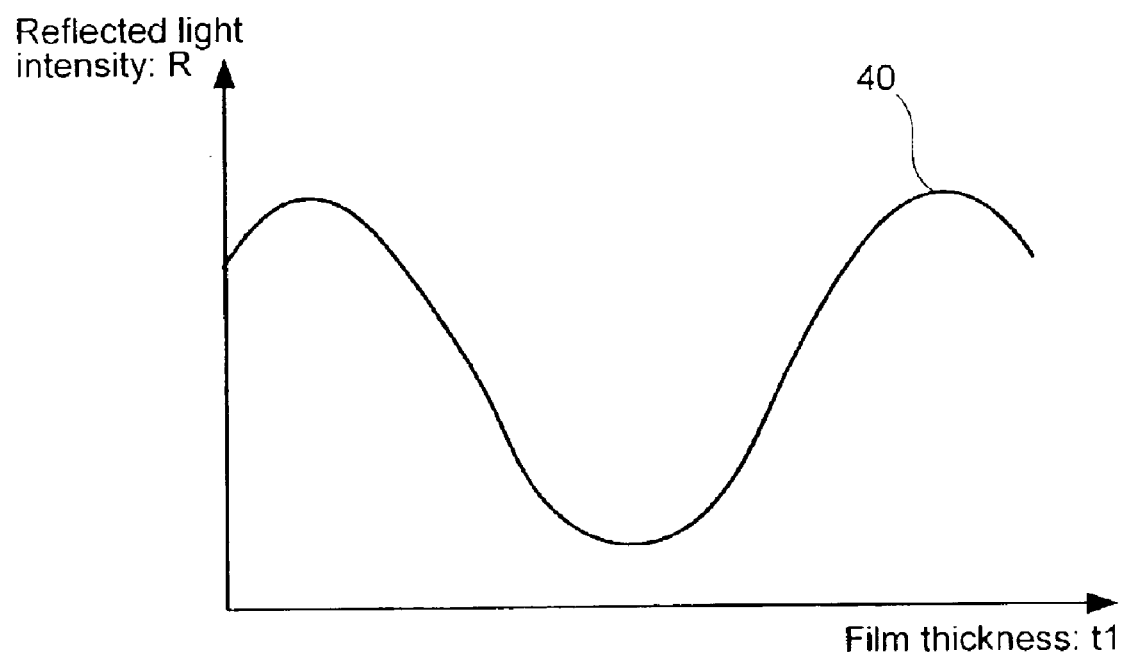
FIG. 7 is a graph which shows changes in the reflected light intensity due to the thin film interference shown in FIG. 6.
Figure 8:
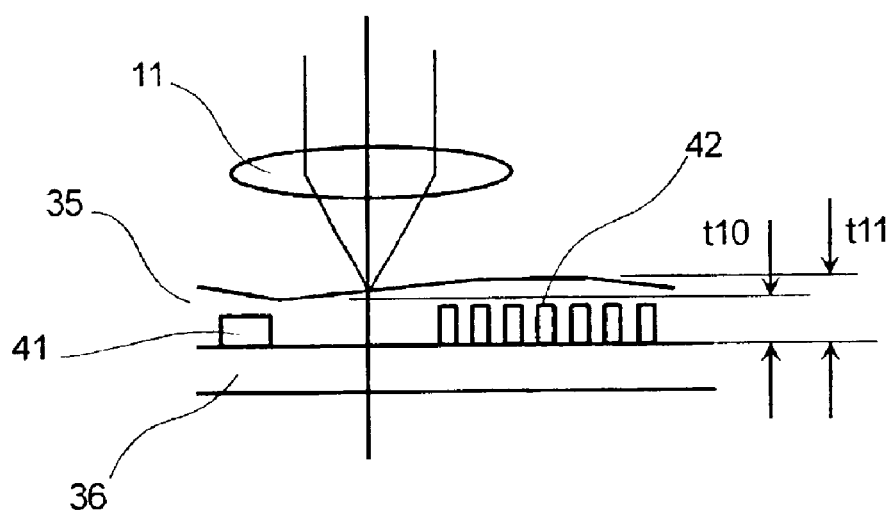
FIG. 8 is a diagrammatic cross section of a sample on which circuit patterns are formed.
Figure 12:
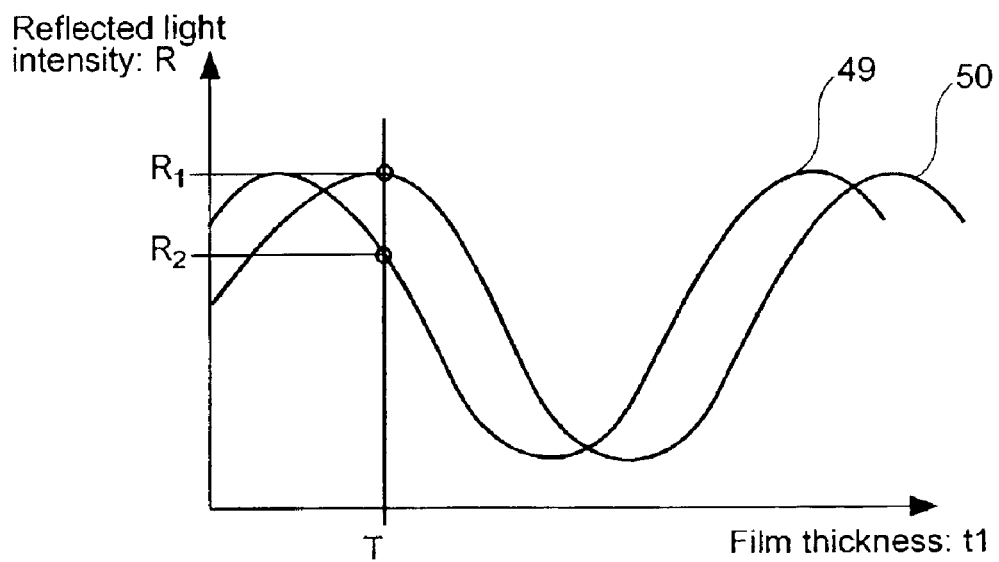
FIG. 12 is a graph which shows changes in reflected light intensity when a light beam strikes the sample at different incident angles.

In this way, the angle of light flux incident on the sample 1 changes as the annular scan diameter of the light flux on the pupil 12 changes. In other words, as shown in FIG. 6 and FIG. 7, when illuminating a sample on which an optically transparent thin film is formed, the reflected light intensity from the sample changes as the angle of the light flux illuminating the sample 1 changes. FIG. 12 shows changes in the reflected light intensity when the incident angle is changed.

For example, when the sample 1 is illuminated with light flux 47, which is caused to annularly scan on the outer portion of the pupil 12, as shown in FIG. 11(a), and changes in the reflected light intensity versus the film thickness are plotted, the result corresponds to a curve 49, as seen in FIG. 12. When the sample 1 is illuminated with the light flux 48, which is caused to annularly scan on the inner portion of the pupil 12, as shown in FIG. 11(b), and changes in the reflected light intensity versus the film thickness are again plotted, the result corresponds to a curve 50, as seen in FIG. 12. As seen in FIG. 12, the waveform phase of the reflected light intensity shifts as the annular scan radius (Pr, Pr2) of the light flux on the pupil 12 is changed. For example, the reflected light intensity at a film thickness of T changes greatly depending on the annular scan radius, that is, the incident angle of the light flux illuminating the sample 1. The reflected light intensity will be R2 when the incident angle is large and R1 when the incident angle is small.

Figure 9:
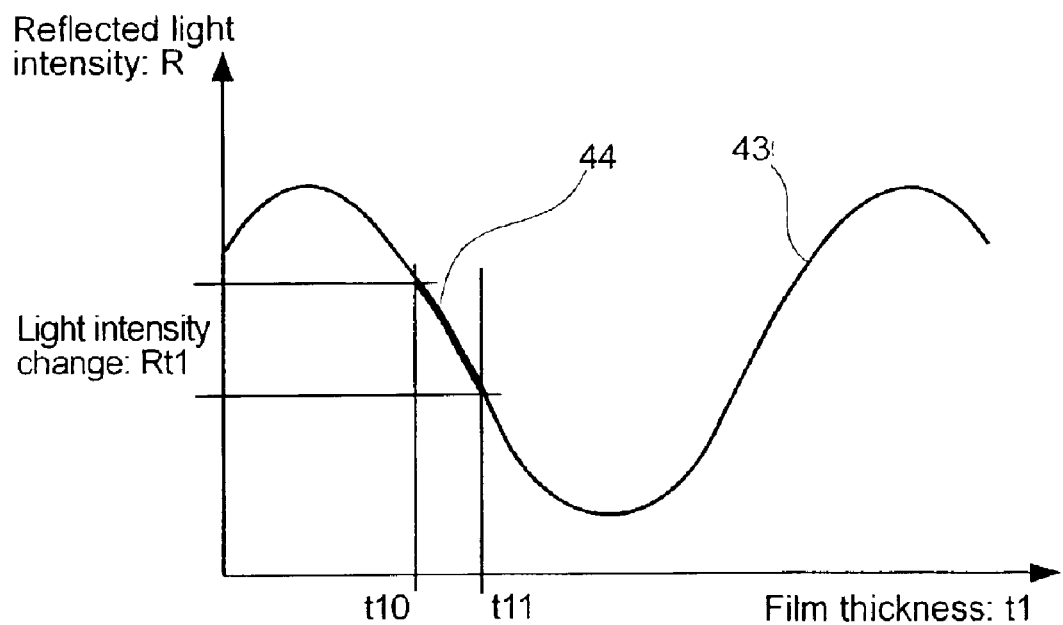
FIG. 9 is a graph which shows thin film interference caused by the circuit patterns shown in FIG. 8.
Figure 10:
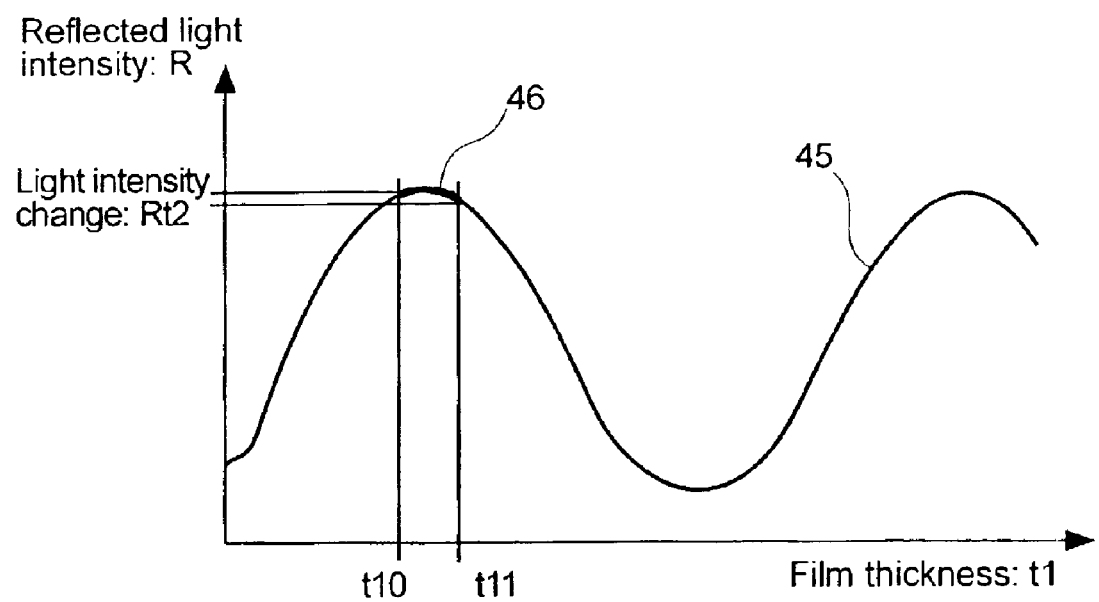
FIG. 10 is a graph which shows thin film interference found in the present invention.

When the sample is illuminated with a light flux that annularly scans on the pupil 12, while keeping the scan radius (the distance from the optical axis of the objective lens 11 to the main beam of the light flux 31) constant, the reflected light intensity from the sample 1 changes in a sinusoidal waveform as a function of the thickness of the optically transparent thin film 35 formed on the sample 1, as shown in FIG. 7. How this reflected light intensity changes depends on the scan radius of the light flux 31 on the pupil 12, as shown in FIG. 12. For example, when the light flux 31 is irradiated on a thin film 35 having thicknesses t01 and t11, the change in reflected light intensity from the sample 1 greatly differs, as shown in FIG. 9 and FIG. 10. When compared to FIG. 9, the change in the reflected light intensity of FIG. 10 is less affected by film thickness variations.

Making use of this property, the thickness range of the thin film 35 formed on the sample 1 is measured beforehand and the scan radius of the light flux 31 on the pupil 12 is set so that the change in the reflected light intensity is minimized within the measured thickness range. This makes it possible to inspect the pattern formed on the sample 1, while reducing adverse affects caused by the thickness distribution of the thin film 35.

The relation between the incident angle and the light intensity is measured by pre-inspection to obtain the relation between the incident angle and the film thickness, and this data is stored in the storage means 21. This measurement can be made by sending an angle instruction to an angle controller 24 from the central processing unit 19 shown in FIG. 1.

Figure 13:
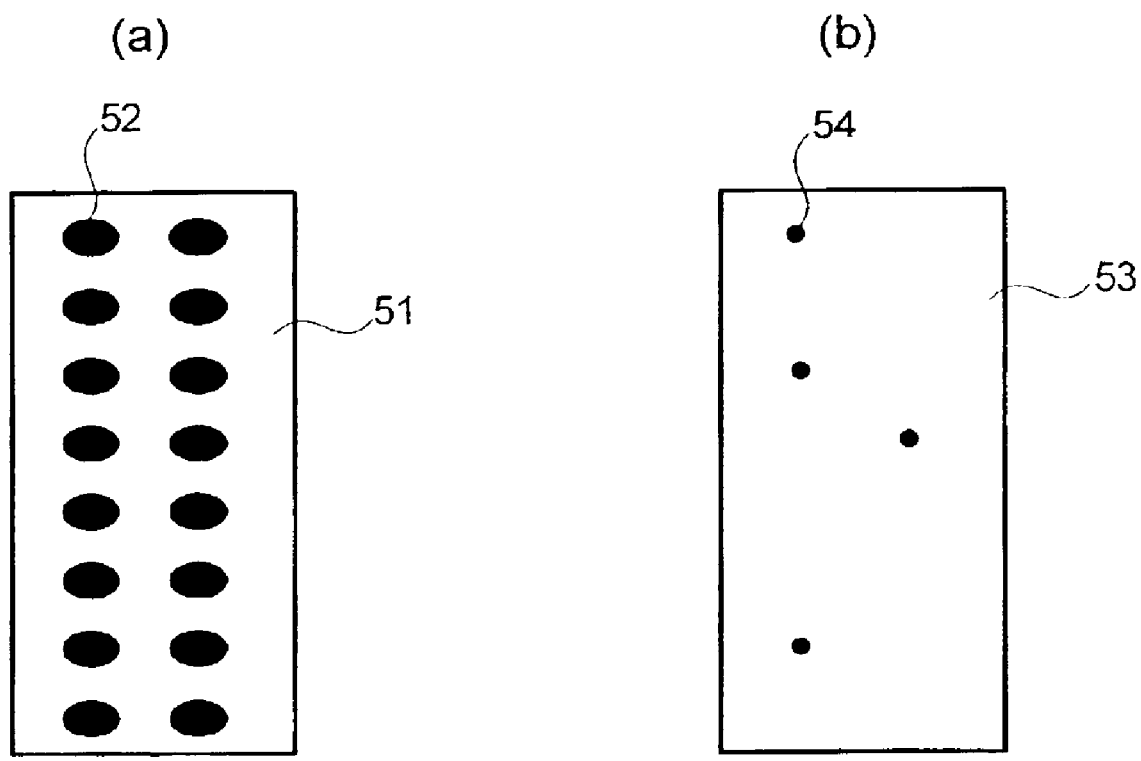
FIG. 13(a) is a schematic diagram showing inspection results obtained without optimizing the incident light angle.
FIG. 13(b) is a schematic diagram showing inspection results obtained with the present invention by optimizing the incident light angle.

FIGS. 13(a) and 13(b) illustrate results obtained by comparing images between chips on the sample 1. FIG. 13(a) is a comparison image obtained by subtracting the output image of the delay memory i7 from the output image of the gray level converter 16. White portions here indicate places where the difference is small, while black portions indicate places where the difference is large. This image was obtained by comparing the images, without taking the change in light intensity between chips into account, so that portions 52 having a larger difference are emphasized. If pattern defect inspection is performed under this condition, the threshold level must be increased to eliminate the black portions, making it impossible to detect actual defects.

On the other hand, FIG. 13(b) shows a comparison image that has been detected after optimizing the incident light angle on the sample 1, as shown in FIG. 10. Since the incident angle of the light illuminating the sample 1 is set so that the change in the reflected light intensity from the sample 1 is minimized within the thickness range of the thin film 35, changes in the light intensity between chips are also minimized. This reduces the difference in the light intensity between the image signals transferred from the gray level converter 16 and the delay memory 17, and extracts the actual defects 54 from the comparison images. Consequently, pattern defects can be detected with high sensitivity.

Figure 14:
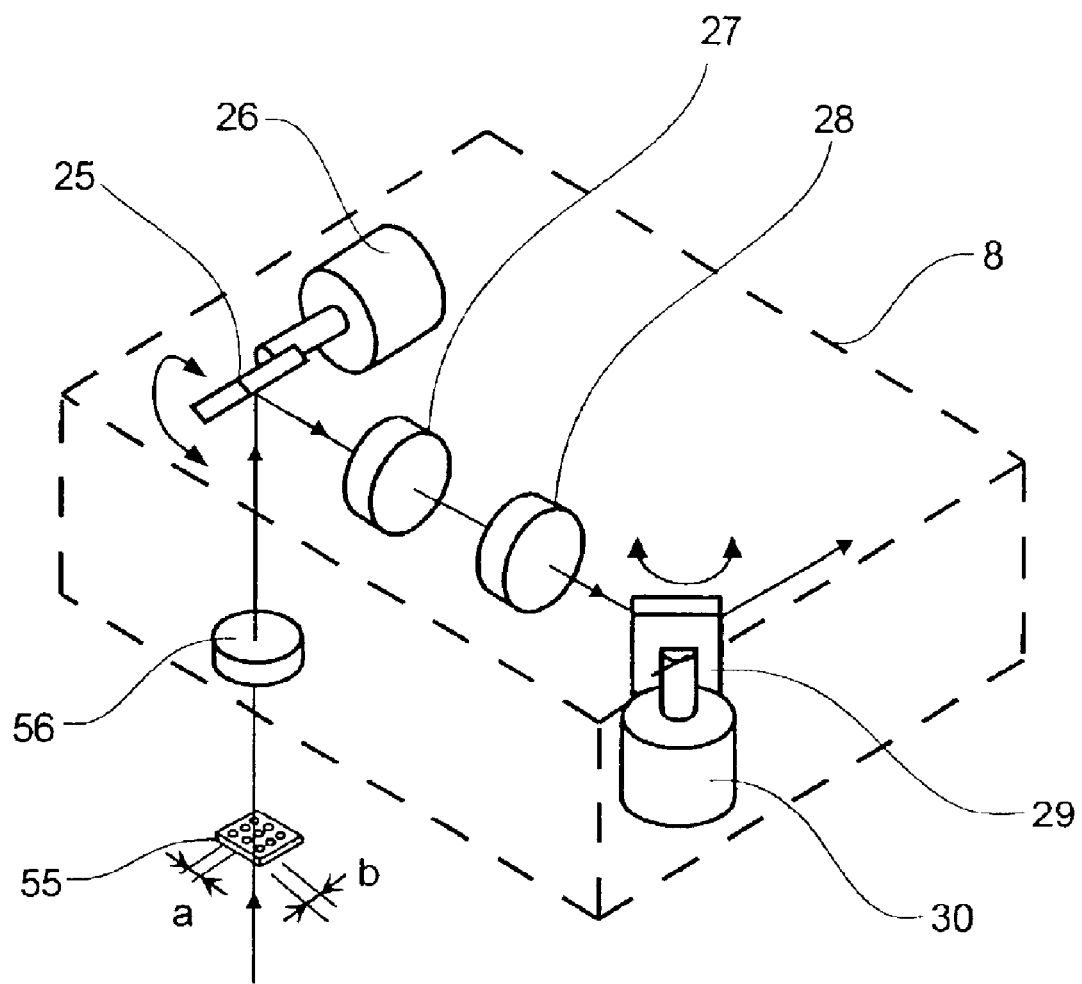
FIG. 14 is a diagram of the light illuminating optical system, including coherence suppression optics, implemented as a second embodiment of the present invention.

Next, another embodiment of the coherence suppression optics 8 will be described with reference to FIG. 14. In this embodiment, the laser beam L1, that has been emitted from the laser light source 5, is irradiated onto a homogenizer 55. The homogenizer 55 forms multiple small light sources arranged in a matrix pattern at an XY pitch of "a" and "b", thereby producing multiple spot light sources from a single light beam. The laser beam L1, after being transformed by the homogenizer 55 into a beam having multiple light spots along the cross section, passes through a lens 56 and strikes a mirror 25. Since the mirror 25 is supported by an oscillating motor 26 that oscillates the mirror 25 within a small angle, the optical axis of the laser beam L1 scans vertically, when reflected from the mirror 25, and then enters a mirror 29 via lenses 27 and 28. The mirror 29 is supported by an oscillating motor 30 that oscillates the mirror 29 within a small angle. The optical axis of the laser beam L1, therefore, scans horizontally when reflected from the mirror 29. The mirror 25 and the mirror 29 are respectively installed at positions conjugate with the focusing position of the objective lens 11.

Figure 15:
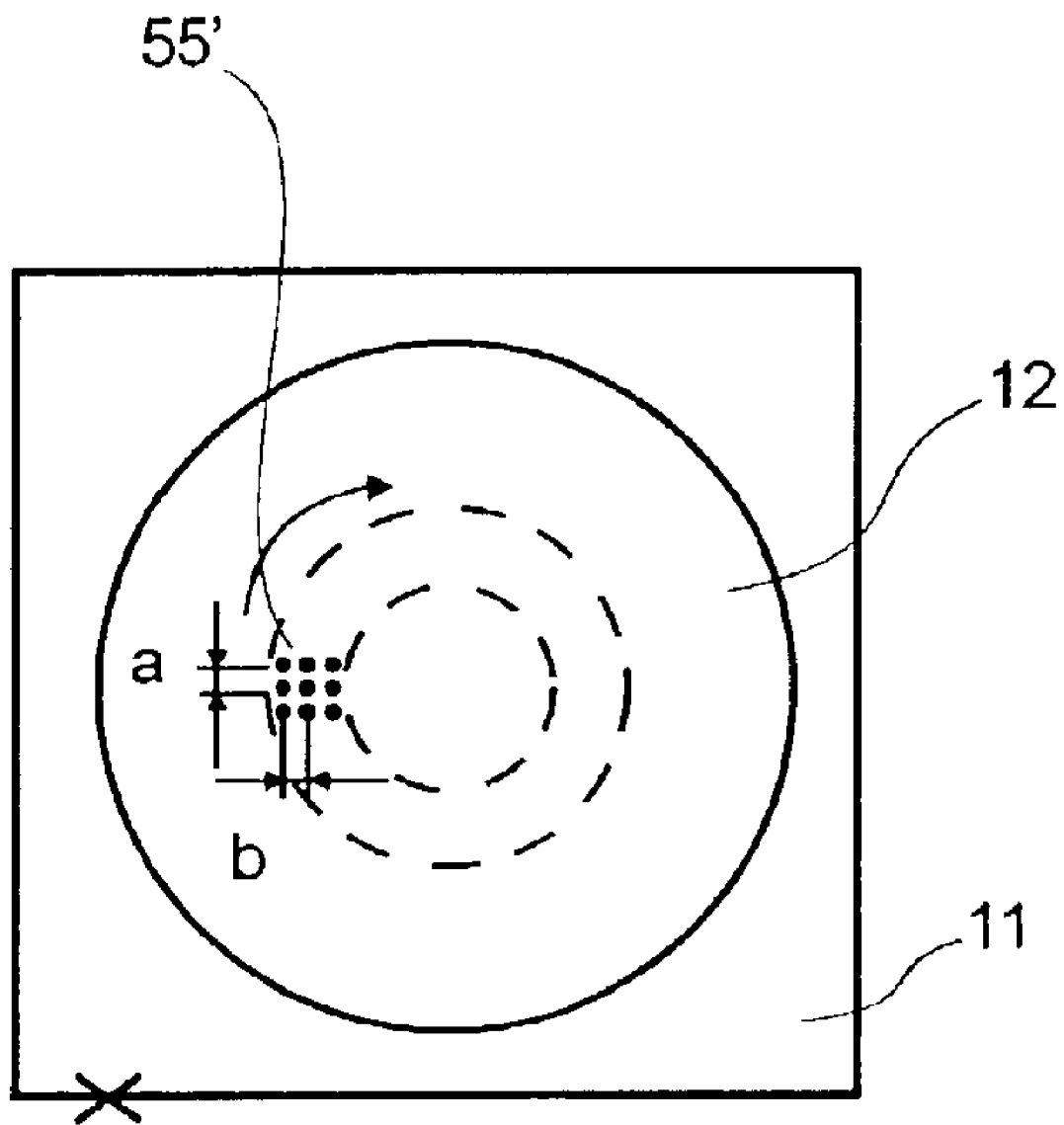
FIG. 15 is a diagram of light flux focused on the pupil of the objective lens after having passed through the optics shown in FIG. 14.

The lenses 56, 27, and 28 are designed and installed so that an image of the homogenizer 55 is focused on the pupil of the objective lens to achieve Koehler illumination. FIG. 15 shows how an image of the homogenizer 55 is focused on the pupil i2 of the objective lens 11. An image 55' of the homogenizer 55, which consists of multiple light spots arranged at an XY pitch of "a" and "b", is focused on the pupil 12 of the objective lens 11. The group of these light spots is rotated circularly within the pupil 12 by the oscillating motors 26 and 30. By changing the amplitude applied to the oscillating motors 26 and 30, the scan diameter within the pupil 12 can be changed, even when using a group of light spots. Thus, this embodiment achieves the same effective results as the aforementioned embodiment.

Figure 16:
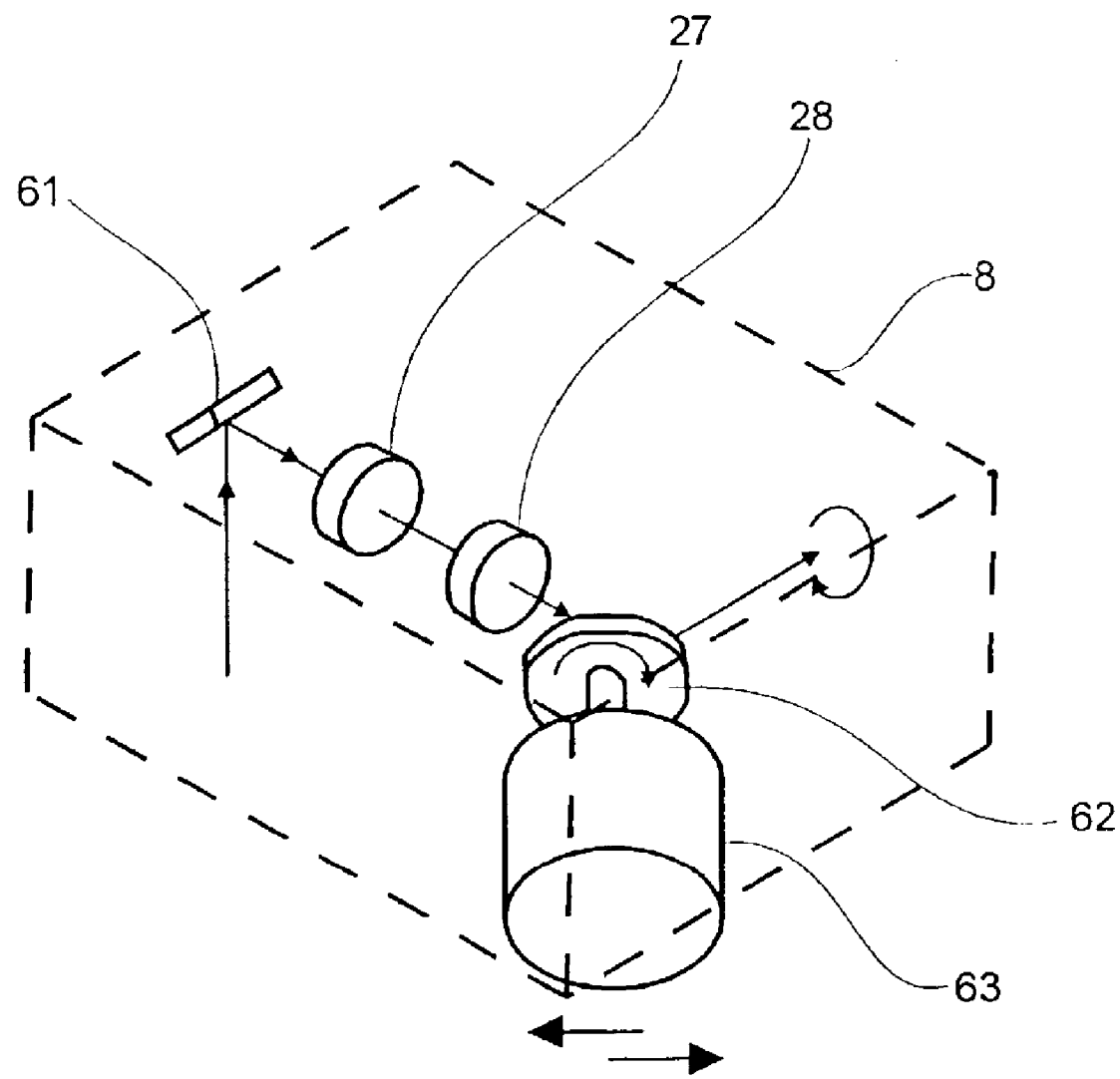
FIG. 16 is a diagram of the light illuminating optical system, including coherence suppression optics, implemented as a third embodiment of the present invention.
Figure 18:
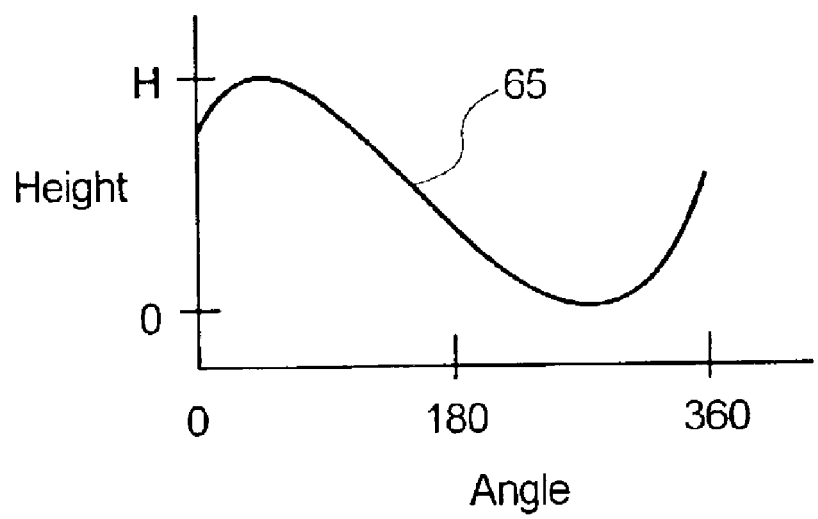
FIG. 18 is a graph which shows a movement track of the mirror shown in FIG. 17.

Another embodiment of the coherence suppression optics 8 will be described with reference to FIG. 16. In this embodiment, the laser beam L1, that has been emitted from the laser light source, is irradiated on a fixed mirror 61, and then it strikes an angular oscillation mirror 62 via lenses 27 and 28. The angular oscillation mirror 62 is supported by a rotating motor 63. FIG. 17(a) and FIG. 17(b) show details of the mirror 62. FIG. 17(a) is a front view, as seen from the reflective surface of the mirror, and FIG. 17(b) is a side view. FIG. 18 shows the movement track of the oscillation mirror 62, when it is rotated, at the position 64 shown in FIG. 17(a). The horizontal axis and vertical axis of FIG. 18 represent the angle and height, respectively. A sine curve 65 corresponds to one rotation of the angular oscillation mirror 62. When a laser beam 67 strikes the angular oscillation mirror 62 at an angle of 45°, the angle of the light reflecting from the position 64 changes, so that a laser beam 68 draws a circular track according to the height of the track 65, as shown in FIG. 18, which corresponds to one rotation of the angular oscillation mirror 62.

Figure 19:
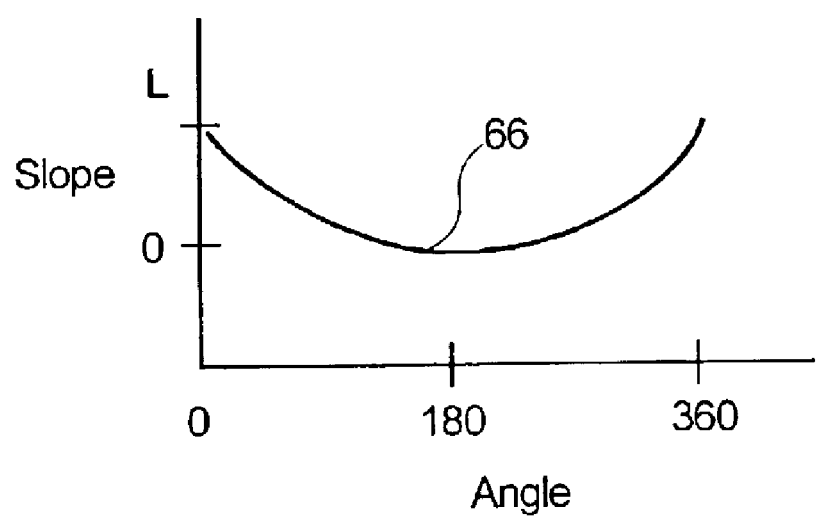
FIG. 19 is a diagram which shows the configuration of a cross section of the mirror shown in FIG. 17.

FIG. 19 shows a cross section of the angular oscillation mirror 62, as seen along a line "A—A" in FIG. 17(a). The mirror 62 has a slope 66 in the horizontal direction. By this slope, the height shown in FIG. 18 changes along the circular arc direction. As shown in FIG. 16, the laser beam irradiation position on the angular oscillation mirror 62 changes as the assembly formed by the angular oscillation mirror 62 and the motor 63 moves in right and left directions, as indicated by arrows in FIG. 16, whereby the laser beam moves along a circular arc with a smaller amplitude near the center of the mirror 62 and a larger amplitude near the edge. The angular oscillation mirror 62 is installed at a position conjugate with the focusing position of the objective lens 11. The diameter of the laser beam movement on the pupil of the objective lens can also be changed by adjusting the position of the rotating motor 63. This embodiment achieves the same effective results as the aforementioned embodiment.

A method of inspecting a circuit pattern formed on a semiconductor wafer to detect defects will be described next with reference to an inspection apparatus equipped with the devices mentioned in the foregoing description of the present invention.

First of all, a wafer 1, that represents a sample to be inspected, is placed on the Z stage 2 and is positioned correctly. Next, the Y stage 4, holding the wafer 1, moves in the Y-axis direction at a constant speed when the stage control circuit 100 receives a signal to drive the stage from a stage position sensor (not shown in the drawing). Meanwhile, the laser beam L1 is emitted from the ultraviolet laser light source 5, and the laser beam diameter is enlarged by the beam expander 7. The laser beam then enters the coherence suppression optics 8 and is output while being scanned by the scanning mirrors 25 and 29 in two intersecting axial directions. The laser beam, that has been emitted from the coherence suppression optics 8, has its optical path shifted at the polarizing beam splitter 10 and enters the objective lens 11. The objective lens 11 condenses the laser beam onto the surface of the wafer 1.

The laser beam, that is scanned in two intersecting axial directions by the scanning mirrors 25 and 29 in the coherence suppression optics 8, scans along a circle on the pupil plane 12 of the objective lens 11. The wafer 1, while being illuminated at the same time, moves at a constant speed in the Y axis direction, while the incident angle of the beam is sequentially changed relative to the normal line direction on the surface of the wafer 1 at each circular scan. The incident angle of the laser beam L1, striking the wafer 1, is determined by the CPU 19, based on the thickness distribution data on the optically transparent thin film formed on the surface of the wafer 1 (measured in advance and stored in the storage unit 21), the relation between the thin film thickness (also measured in advance and stored in the storage unit 21) and the reflected light intensity obtained for each incident angle of the laser beam L1 on the wafer 1, and the position information indicating the position of each stage as measured by stage position sensors (not shown in drawing) for the X stage 3 and Y stage 4. Using these results, the oscillating motors 26 and 30 are controlled by the angle control means 24 in order to control the amount of oscillation of the mirrors 25 and 29.

The wafer 1 is illuminated with a laser beam at an incident angle according to the thickness of the optically transparent thin film formed over the surface of the wafer 1. The light reflected from the wafer 1 is condensed by the objective lens 11 and focused on the TDI sensor 14 by a lens 13.

As mentioned above, the TDI sensor i4 is a time delay integration image sensor that is made up of a number of linear image sensors connected in a multiple stage array. The image signals detected at each stage of the linear image sensors are sequentially transferred to the linear image sensor of the next stage and accumulated. This transfer timing is synchronized with the movement of the Y stage 51, which is constantly detected by the stage position sensor.

A grayscale image signal 14a of the wafer 1, that is acquired with the TDI sensor 14, is converted into a digital signal. by the A/D converter 15. Uneven brightness or shading on the image, that has been caused by interference of the laser beam with the thin film formed on the wafer 1 under test, is corrected with the gray level converter 16. The signal processed by the gray level converter 16 is divided into two signals. One is stored in the delay memory 17, and the other is input to the comparator 18.

In the comparator 18, the comparison image 11, that has been transferred from the gray level converter 16, and the reference image Ir, that was detected in the previous step (adjacent chip or adjacent pattern) and stored in the delay memory 17, are both input to the positioning circuit 181. The positioning circuit 181 finds the positional shift (deviation) between the comparison image 11 and the reference image Ir and corrects this shift.

The positioning circuit 181 outputs the comparison image 11 and the reference image Ir after correcting their mutual positional shift (deviation) and inputs them to the differential image detection circuit 182, where a differential image Id representing the difference between the two images is obtained. The differential image Id obtained here is sent to the mismatch detection circuit 183, and it is compared with a preset threshold level. Portions higher than this threshold level are detected as defects. The information about the defects is then sent to the feature extraction circuit 184.

The feature extraction circuit 184 extracts information about the area, length and coordinates of the defects detected by the mismatch detection circuit 183, and it sends the information to the central processing unit (CPU) 19. The central processing unit 19 stores the information about the defects in the memory unit 21, and it also displays this information on the screen of the display means 22. Though not shown in FIG. 1 and FIG. 3, the comparison image 11, that was transferred from the gray level converter 16 and whose positional shift was corrected by the positioning circuit 181, is also input to the central processing unit 19 and stored in the memory unit 21, or displayed as an image containing defects on the screen of the display means 22, as needed. Information about defects stored in the memory unit 21 can be transferred via communication lines from the output means 23 to other devices, such as review (evaluation) devices used to observe a detailed view of the defects.

Figure 22:
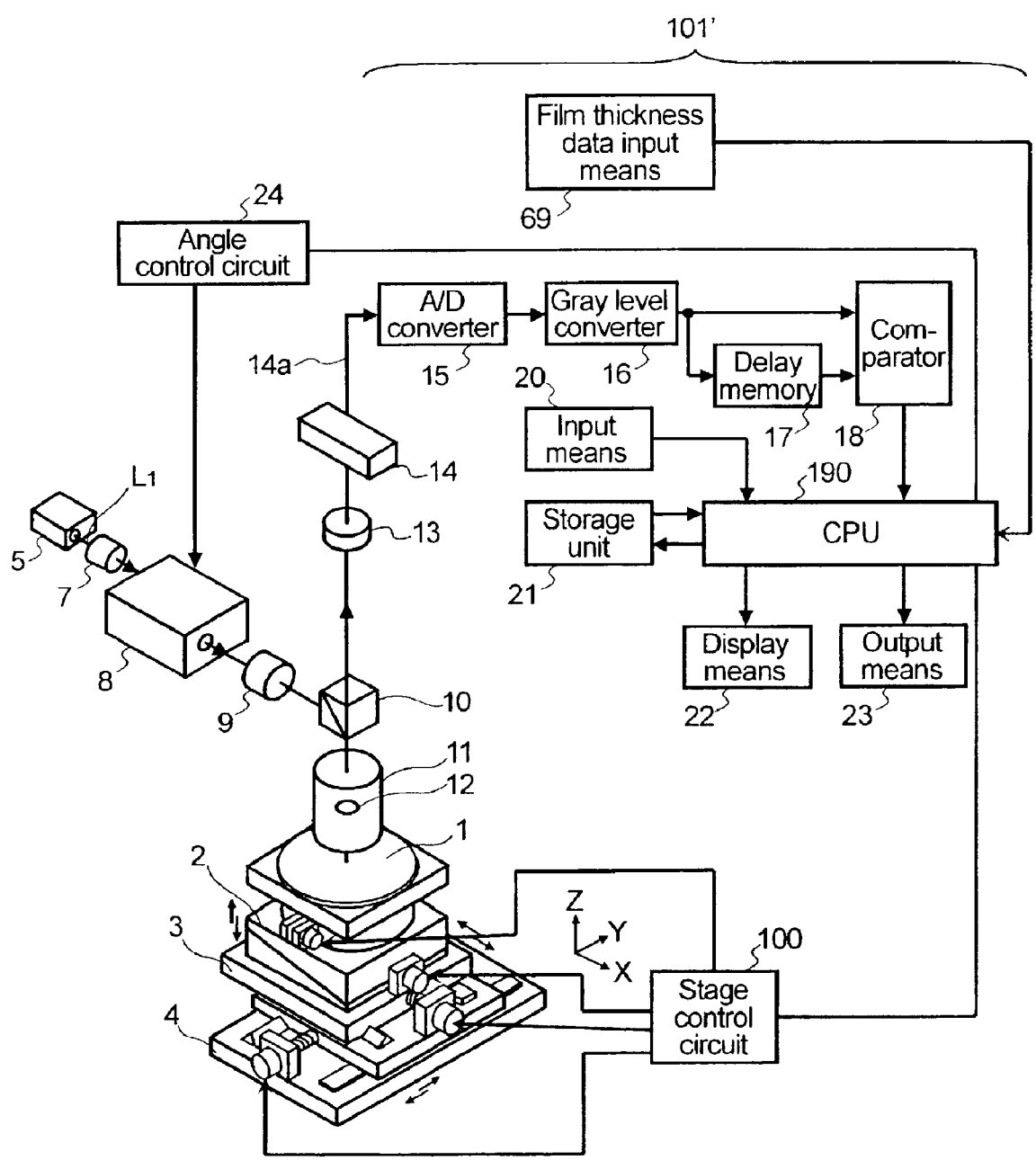
FIG. 22 is a schematic diagram showing a pattern defect inspection apparatus representing a second embodiment of the present invention.

Next, a second embodiment of the invention will be described with reference to FIG. 22. The basic components of this second embodiment are identical with those of FIG. 1, except that the image processing circuit 101 has a slightly different configuration. This embodiment uses a film thickness data input means that transfers film thickness data 69 to the central processing unit 190 of the image processing circuit 101.

The operation of this embodiment will be described. In FIG. 1, inspection is performed, after finding an optimum incident angle, by measuring the relation between the film thickness and the reflected light intensity during a pre-inspection process. In this embodiment, however, the thickness of the film on the sample 1 is measured in advance with a thickness gauge, etc., and the film thickness data 69 is input to the central processing unit 190. The central processing unit 190 processes the film thickness data 69 and supplies an instruction to the angle control circuit 24 according to the thickness of the optically transparent thin film coated over the sample 1, so that the sample is illuminated with light at an optimum incident angle and the image thus acquired is used for pattern inspection. This second embodiment yields the same effective results as the first embodiment.

Figure 23:
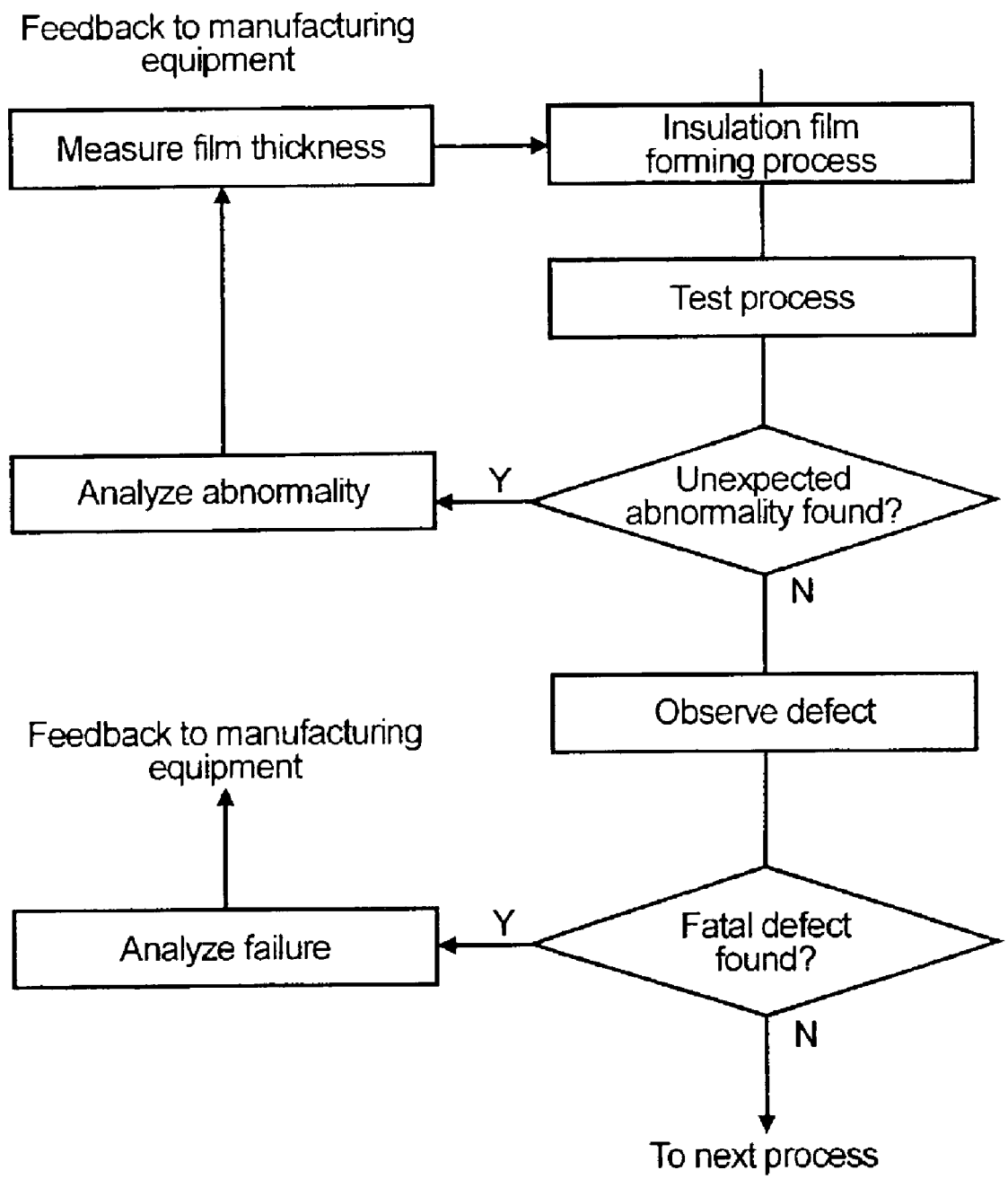
FIG. 23 is a flowchart of process control using the pattern inspection of the present invention.

When the light intensity changes during an inspection carried out according to the invention, even after setting the optimum incident angle of illumination light and the inspection results fluctuate significantly, this is an indication that a sudden increase in film thickness variations on the sample has probably occurred. By checking the inspection results, sudden variations in the film thickness of the sample can be monitored to allow process control. FIG. 23 shows a flow-chart for process control using the pattern inspection of the invention. If abnormal results are found in the test process, that sample is then removed, and the film thickness is re-measured with a thickness gauge to investigate the cause. The results are then fed back to the film deposition or forming equipment, when needed.

As described above, the invention is capable of reducing adverse effects from thin film interference, by illuminating the sample with a laser beam at an optimum incident angle according to the thickness of the thin film formed on the sample. This invention is therefore capable of canceling out light intensity fluctuations, that may occur during inspection, due to thickness variations of the thin film caused by a difference in the circuit pattern density or thickness variations of thin films among chips that occur depending on sample positions. Pattern inspection can therefore be performed with high sensitivity.

The invention is also effective in providing process control when sudden fluctuations in the light intensity are detected during inspection.

The invention may be embodied in other specific forms without departing from the spirit or essential characteristics thereof. The present embodiment is therefore to be considered in all respects as illustrative and not restrictive, the scope of the invention being Indicated by the appended claims, rather than by the foregoing description, and all changes which come within the meaning and range of equivalency of the claims are therefore intended to be embraced therein.

What is claimed is:

1. A method of detecting pattern defects, comprising:
   annularly scanning a laser beam emitted from a laser light source on a pupil of an objective lens;
   illuminating said scanned laser beam onto a sample on which there is formed a pattern coated with an optically transparent thin film, through said objective lens;
   acquiring an optical image of said illuminated sample; and
   processing said acquired image to find defects in said pattern;
   wherein the annular scan diameter of said laser beam is determined based on the thickness of said optically transparent thin film.

2. The method of inspecting pattern defects, according to the claim 1, wherein the wavelength of said laser beam illuminating said sample is in the ultraviolet region.

3. The method of inspecting pattern defects, according to the claim 1, wherein the wavelength of said laser beam illuminating the sample is from 100 to 355 nanometers.

4. A method of inspecting pattern defects, comprising:
   annularly scanning a laser beam emitted from a laser light source on a pupil of an objective lens;
   illuminating said scanned laser beam on a pattern, which is formed on said substrate and is covered with an optically transparent thin film, while said substrate is held on a table which is continuously moving along one direction;
   acquiring an optical image of said pattern that is illuminated with said laser beam in synchronization with the annular scan of said laser beam; and
   processing the acquired image to find defects in said pattern;
   wherein the annular scan diameter of said laser beam is determined based on the thickness of said optically transparent thin film.

5. The method of inspecting pattern defects, according to the claim 4, wherein said laser beam illuminating said pattern is in the ultraviolet wavelength region.

6. The method of inspecting pattern defects, according to the claim 4, wherein the laser beam illuminating said pattern has a wavelength ranging between 100 and 355 nanometers.

7. An apparatus for inspecting pattern defects, comprising:
   a laser light source;
   a scanning device that scans a laser beam emitted from said laser light source;
   an illuminating means that irradiates said scanned laser beam onto a sample, having a pattern which is coated with an optically transparent thin film, using an objective lens;
   an imaging device that uses an objective lens to acquire an optical image of the pattern of said sample that is illuminated with said laser beam; and
   an image processing means that find defects in said pattern by processing an image of said sample acquired with said imaging device;
   wherein said scanning device annularly scans said laser beam on the pupil plane of said objective lens, and the annular scan diameter is determined based on the thickness of said optically transparent thin film.

8. The apparatus for inspecting pattern defects, according to the claim 7, wherein said laser light source emits light in the ultraviolet wavelength region to illuminate said pattern.

9. The apparatus for inspecting pattern defects, according to the claim 7, wherein said laser light source emits light having a wavelength between 100 and 355 nanometers to illuminate said pattern.

10. The apparatus for inspecting pattern defects, according to the claim 7, wherein said imaging device has a time delay integration sensor to acquire an optical image of said pattern.

11. An apparatus for inspecting pattern defects, comprising:
    light illuminating optics having a laser light source and an objective lens;
    a table on which a substrate is placed and which is capable of moving along at least one direction;
    a scanning device to annularly scan a laser beam emitted from said laser light source on a pupil plane of the objective lens of said light illuminating optics;
    an imaging device that acquires, in synchronization with the annular scan of said laser beam, an optical image of said substrate while said substrate is held on said table and is illuminated by the annularly scanned laser beam through said light illuminating optics;
    an image processing means that detects defects in said pattern by processing an image acquired with said imaging device; and
    a control means which determines the annular scan diameter of said laser beam and sends information about said diameter to said scanning device.

12. The apparatus for inspecting pattern defects, according to the claim 11, wherein said control means determines said annular scan diameter based on the thickness of an optically transparent thin film coated over a pattern formed on said substrate.

13. The apparatus for inspecting pattern defects, according to the claim 11, wherein said laser light source illuminates said sample with light in the ultraviolet wavelength region.

14. The apparatus for inspecting pattern defects, according to the claim 11, wherein said laser light source illuminates said sample with light having a wavelength between 100 and 355 nanometers.

15. The apparatus for inspecting pattern defects, according to the claim 11, wherein said imaging device uses a time delay integration sensor to acquire an optical image of said pattern.

* * * * *